United States Patent [19]

Charlton et al.

[11] Patent Number: 4,776,904
[45] Date of Patent: Oct. 11, 1988

[54] MULTILAYER ANALYTICAL ELEMENT AND METHOD OF MAKING, USING ULTRASONIC OR LASER ENERGY

[75] Inventors: Steven C. Charlton, Elkhart; Bert Walter, South Bend, both of Ind.

[73] Assignee: Miles Inc., Elkhart, Ind.

[21] Appl. No.: 756,676

[22] Filed: Jul. 19, 1985

[51] Int. Cl.⁴ .................... G01N 31/22; B32B 31/16; B32B 31/18

[52] U.S. Cl. .................... 156/73.1; 156/73.3; 156/272.8; 422/56; 435/805

[58] Field of Search .................... 422/55, 56, 57; 493/341; 156/73.1, 73.3, 272.8; 53/DIG. 2; 435/805

[56] References Cited

U.S. PATENT DOCUMENTS

| Re. 30,267 | 5/1980 | Bruschi | 422/56 X |
| 3,989,778 | 11/1976 | Osborne | 156/272.8 X |
| 3,992,158 | 11/1976 | Przybylowicz | 422/57 |
| 3,993,451 | 11/1976 | Verbeck | 422/57 |
| 4,061,468 | 12/1977 | Lange et al. | 422/56 |
| 4,230,757 | 10/1980 | Toner | 156/73.1 X |
| 4,478,661 | 10/1984 | Lewis | 156/73.1 X |
| 4,543,154 | 9/1985 | Reiter | 156/73.1 |
| 4,678,640 | 7/1987 | Hamano et al. | 422/58 X |

FOREIGN PATENT DOCUMENTS

| 1060266 | 5/1976 | Japan | 156/73.3 |
| 1046671 | 10/1966 | United Kingdom | 156/73.1 |
| 1121057 | 7/1968 | United Kingdom | 156/272.8 |
| 1128399 | 9/1968 | United Kingdom | 156/73.1 |

Primary Examiner—Michael S. Marcus
Assistant Examiner—Jill Johnston
Attorney, Agent, or Firm—Roger N. Coe

[57] ABSTRACT

A method of making a multilayer analytical test element comprises providing layers at least one of which is responsive to detect a ligand in a liquid sample, or to detect the ligand binding capacity of the sample, and at least one other layer that is fusible when subjected to sonic energy, arranging the layers one on top of the other together to form a composite blank of layers, subjecting the composite to ultrasonic or laser energy to cut the composite to the desired dimension of the test element and to simultaneously weld the layers at the edges thereof, said energy softening and fusing the fusible layer to thereby bond the layers together.

3 Claims, 1 Drawing Sheet

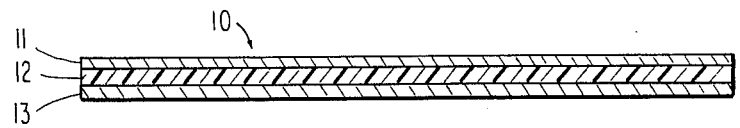
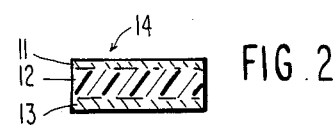
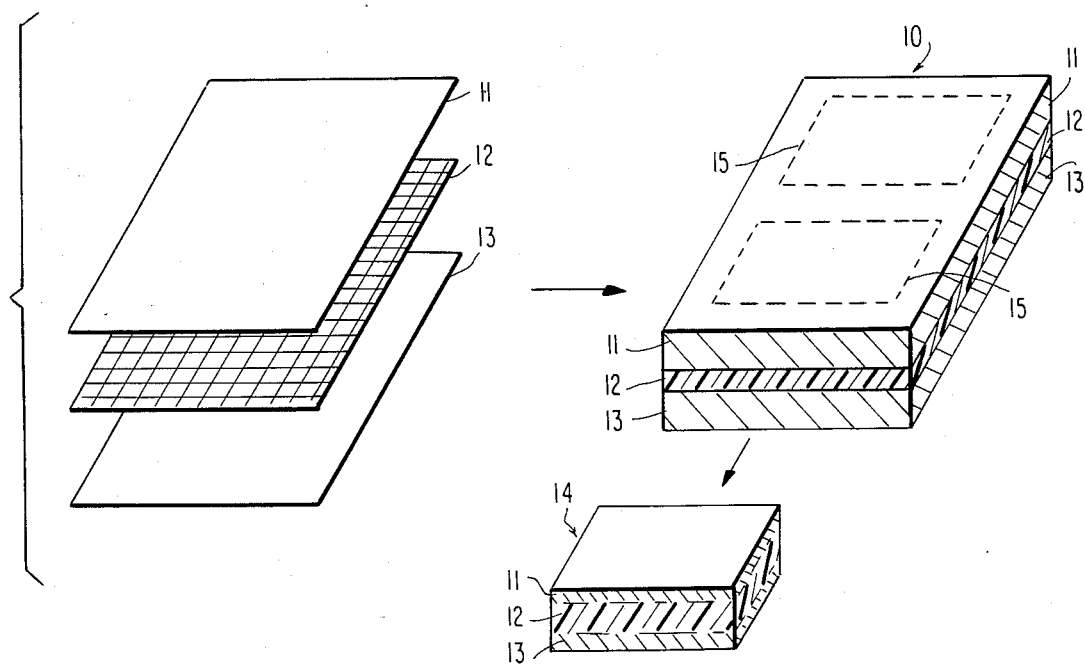
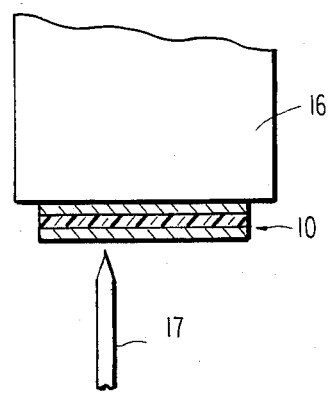

MULTILAYER ANALYTICAL ELEMENT AND METHOD OF MAKING, USING ULTRASONIC OR LASER ENERGY

INTRODUCTION AND BACKGROUND OF THE INVENTION

The present invention relates to the field of analytical test elements and methods of making same using ultrasonic or laser energy.

The art of analytical chemistry has been greatly advanced since biochemistry began emerging as a primary scientific frontier, requiring increasingly sophisticated analytical methods and tools to solve problems, the solutions to which were never before attempted. Likewise, the medical profession has lent impetus to the growth of analytical chemistry, emphasizing both high precision and speed in obtaining results. The remarkable progress that has occurred in analytical chemistry has been still further spurred by industries such as brewing, chemical manufacturing, and the food industry.

To satisfy the needs of these expanding technologies, a myriad of analytical procedures, compositions and apparatuses has evolved, including solution chemistry techniques, automated machinery and the so-called reagent test strips. It is to the last of these that the present invention is primarily directed. The reagent strip devices are useful in manual and automated diagnostic systems, and, more particularly, multilayer analytical elements are useful in the qualitative and quantitative determination of body fluid constituents and medicaments present in such body fluids.

Test devices in the form of test strips and similar solid state analytical elements have become commonplace in the analysis of various types of samples, particularly biological fluids. Test strips designed for detecting clinically significant substances in biological fluids, such as serum and urine, have been advantageous in the diagnosis of disease and have enabled more prompt treatment of a variety of conditions.

Reagent strip test devices enjoy wide use in many analytical applications because of their relatively low cost, ease of utilization and speed in obtaining results. In medicine, for example, numerous physiological functions can be monitored merely by dipping reagent strips into a sample of body fluid, such as urine, and observing a detectable response such as a change in color or a change in the amount of light reflected from or absorbed by the strip.

Test strips of various types have been known and used for many years in a wide variety of fields, from the most familar pH test paper devices to in vitro diagnostic devices for glucose, protein, occult blood and the like (see U.S. Pat. Nos. 3,164,534; 3,485,587 and 3,012,976). Reagent compositions found in such test strips, often having limited sensitivity, interact with the constituent or constituents to be determined by direct chemical reaction and are applied to the detection of substances that may be present in liquid samples in very small amounts.

With regard to such reagent test strips, many different chemical reactions have been devised for detecting body fluid components. Many of these reactions produce a detectable response which is quantitative or at least semiquantitative. Thus, by measuring the response after a predetermined time, the analyst can obtain not only a positive indication of the presence of a particular constituent in a test sample, but also an estimate of how much of the constituent is present. Such strips provide the physician with a facile diagnostic tool as well as the ability to gauge the extent of disease or body malfunction.

Test devices usually comprise one or more carrier matrices, such as absorbent paper, having incorporated with them a particular reagent or reactant system which manifests some change, typically color, in the presence of a specific test sample component. Depending on the reactant system incorporated with a particular matrix, these devices can detect the presence of glucose, ketone bodies, bilirubin, urobilinogen, occult blood, nitrite, and other substances. The specific color change and the intensity of the color observed within a specific time range after contacting the strip with the sample is indicative of the presence of a particular component and its concentration in the sample. Some of these test devices and their reactant systems are set forth in U.S. Pat. Nos. 3,123,443; 3,212,855; 3,814,668; 3,164,534; 2,981,606; 3,298,789; and 3,092,465.

A basic multilayer integral analytical element is described in U.S. Pat. No. 3,092,465. Such multilayer elements use an absorbent carrier impregnated with one or more reagents, typically including a color former, over which is coated a semipermeable membrane. Upon contact with a test liquid, analyte passes through the membrane and into the carrier to generate color in an amount related to the concentration of analyte. The membrane prevents passage and absorption of certain interfering components such as red blood cells, that could impair accurate reading of the color provided as a test result.

Other multilayer integral analytical elements are described in U.S. Pat. No. 3,992,158. Such elements can receive a liquid sample and spread the sample within a spreading layer of the element to obtain in the element an apparent uniform concentration of analyte and produce in the presence of analyte an analytical result that can be measured quantitatively by automated devices, using techniques such as spectrophotometry, fluorimetry, etc.

Test strips are disclosed in U.S. Pat. No. 3,802,842 made by adhering a test layer to a carrier layer by an adhesive material and covering the layers with a mesh. The mesh is heated by various ways, including ultrasonically to bond the mesh layer to the adhesive layer. The layered material is thereafter cut into test strips of the desired size by conventional means. In U.S. Pat. No. 4,061,468, a test strip is shown which is formed by sealing test papers between a synthetic resin film and a mesh and thereafter, in a separate step cutting the laminate into the desired strip width.

Many of the prior known test strips have more than one reagent-bearing carrier matrix or layer. Thus, a reagent strip can contain tests for more than one constituent in a particular liquid sample. For example, a single reagent strip can consist of a reagent-bearing carrier matrix responsive to glucose in urine, and another matrix layer spaced from the first but adjacent thereto and responsive to ketones, such as acetoacetate. Such products are known on the market. Another reagent strip now being marketed contains eight adjacent reagent-incorporated matrices and provides analytical measurements of pH, protein, glucose, ketones, bilirubin, occult blood, nitrite and urobilinogen.

The devices of the prior art have been made by many different techniques, such as by impregnating paper layers, by printing or spraying the reagent composition onto a layer of the carrier material, or by forming films which are solidified.

Where the reagent layer comprises multiple layers, such layers can be maintained in laminar relationship by adhesives which permit fluid passage between layers. It is not always necessary to employ adhesive to adhere one reagent layer to another. In preparing integral analytical elements using film formers, the layers can be preformed separately and laminated to form the overall element. The material of the film layer can be a composition comprising a plasticizer and a polymer suitable to impart dimensional stability. Layers prepared in such a manner are typically coated from solution or dispersion onto a surface from which the dried layer can be physically stripped.

Blush polymer layers can be used as the film layer material. The film is formed on a substrate by dissolving a polymer in a mixture of two liquids, one of which is of a lower boiling point and is a good solvent for the polymer and the other of which is of a higher boiling point and is a nonsolvent or at least a poor solvent for the polymer. Such a polymer solution is then coated on the substrate, and dried under controlled conditions.

The thickness of any reagent layer and its degree of permeability are widely variable and depend on actual usage. Dry thicknesses of from about 5 microns to about 100 microns have been convenient, although more widely varying thickness may be preferable in certain circumstances.

It may be advantageous to incorporate one or more surfactant materials, such as anionic and nonionic surfactant materials, in the reagent layers. They can, for example, enhance coatability of layer formulations and enhance the extent and range of wetting in layers that are not easily wetted by liquid samples in the absence of an aid such as a surfactant.

In general, the present invention deals with the formation of analytical elements, typically multilayer test elements, for detecting a ligand in, or the ligand binding capacity of, a ligand sample. The general structure of such elements includes one or more reagent impregnated layers incorporating a reagent that is responsive to the ligand in the sample, or responsive to the ligand binding capacity of the sample to give a detectable response and a support layer. Other layers can also be present such as spreading layers, radiation diffusing or blocking layers and the like.

The term "ligand" as used herein refers to body fluid constituents and medicaments or other substances present in such body fluids. The following exemplifies a number of such possible ligands. Reagent compositions are known for blood, plasma or serum ligands such as ascorbic acid, bile acids, bilirubin, cholesterol, creatinine, glucose, lactic acid, phospholipids, triglycerides, urea nitrogen (BUN) and uric acid. Also important is the determination of blood chemistry enzyme ligands such as amylase, cholinesterase, creatine phosphokinase (CPK), the dehydrogenases (hydroxybutyric, isocitric, lactic and malic), lipase, phenylalanine, the transaminases (glutamic oxaloacetic and glutamic pyruvic acid), and alkaline phosphatases, gammaglutamyl transpeptidase, leucine aminopeptidase and the erythrocyte enzymes (glucose-6-phosphate dehydrogenase, 6-phosphogluconate dehydrogenase, glutathione reductase and pyruvate kinase). Testing is also possible for blood protein ligands such as albumin, cryoglobins, components of the coagulation and fibrinolytic systems, complement factors and the cellular and serum immune effectors such as interferon and immunoglobins.

Likewise, reagent compositions are known for urine chemistry determinations. In the field of urine chemistry such ligands generally include ascorbic acid, albumin, creatine, creatinine, glucose, bile acids, bilirubin, protein, ketones, occult blood, nitrite, amylase and phenylpyruvic acid. Further details with respect to ligands will be found in U.S. Pat. No. 4,390,343.

SUMMARY OF THE INVENTION

Briefly stated, the present invention comprises a test device and method for making. The device comprises a multilayer analytical test element comprising a plurality of layers, at least one of which is a responsive layer i.e., is responsive to detect a ligand in a liquid sample, or to detect the ligand binding capacity of the sample, to give a detectable response, and at least one other layer (and normally at least two layers) which is composed of fusible material and which is positioned adjacent to said responsive layer. It is an important feature of this invention that the said layers have been bonded together using ultrasonic or laser energy to cut said element from a composite blank of said plurality of layers and simultaneously weld these layers together at their cut edges.

A further feature of the invention resides in a method of making the test elements by forming a composite blank which is an unadhered assembly containing a plurality of layers, including a ligand responsive layer and a fusible layer. The fusible layer is capable of melting and fusing to bond to at least one adjacent layer. The composite blank is then simultaneously cut and welded utilizing an ultrasonic or laser energy cutting device. In carrying out the invention with precisely focused ultrasonic or laser energy, the composite blank is subjected to the cutting and welding action simultaneously along a sharply focused cutting line. The fusible layer is melted along the cutting edge of the laser or ultrasonically generated energy to bond said fusible layer to said layer which is ligand responsive and at the same time cut the test strip into the desired dimension. The laser or ultrasonic cut has a finite width and enables a sharp and clearly defined cut to be made on the composite blank to permit the test elements to be cut according to desired dimensions. The fusible layer softens at the cutting edge only and therefore bonds to the adjacent layers at their respective edges only. Since the edges of the reagent matrices are sealed runover from one test matrix to another on the same test device is prevented or substantially reduced thereby improving the results obtained, especially on test devices in which incompatible reagents are present in adjacent matrix areas of the same test device.

In one preferred embodiment, the ligand responsive layer is sandwiched between two fusible layers.

The analytical test element of the invention can additionally include an inert base support member, holder or substrate. At least one, preferably two, indicator layer members, or ligand responsive members, are bonded to one or more fusible layer in the manner described above. The indicator member or ligand responsive layer can be any of the configurations referred to above and described in the art. A plurality of such ligand responsive layers can be used. the test element means of the present invention can take on many forms. The ligand responsive function can be carried out by a wide variety of combinations of different layers such as a layer of absorbent material, a substantially liquid-impervious layer, and a reagent layer overlaying at least one of the liquid-impervious layers. Many combinations are known in the art and some of these are referred herein above. Any suitable layer or combination of layers can be used for purposes of this invention for the ligand response layer and any suitable supporting substrate or carrier layer, usually inert, can be used for the support.

BRIEF DESCRIPTION OF THE DRAWINGS

The invention is further illustrated in the drawings wherein:

FIG. 1 shows an enlarged schematic side view of a composite blank of unadhered layers used to prepare reagent test strips and depicts the several layers in their unbonded condition prior to cutting and fusing;

FIG. 2 shows an enlarged schematic side view of a reagent test strip after having been cut from the composite blank of FIG. 1 having two indicator members and a middle layer of fusible material bonding the two outer layers together;

FIG. 3 is an isometric schematic view of the sequences of carrying out the present invention to prepare the test strips which are cut and welded by ultrasonic or laser energy means; and FIG. 4 is a schematic diagram of the apparatus for cutting and welding by ultrasonic energy.

DETAILED DESCRIPTION OF THE INVENTION

Test devices as presently disclosed herein can be formulated to respond to a myriad of analysates, depending on anticipated use. Indicators known in the art can be provided for test sample constituents such as glucose, pH, nitrite, occult blood, bilirubin, urobilinogen, protein, ketone and others as will be apparent from the foregoing. Thus, the present invention lends itself to the detection of many possible liquid sample constituents.

Referring to FIG. 1, a composite blank 10 can be prepared from a plurality of individual layers 11, 12 and 13. In the embodiment illustrated, layers 11 and 13 are paper or fibrous based layers which typically contain a reagent responsive to a ligand in a test sample, or responsive to the ligand binding capacity of the test sample, to give a detectable response. These layers are referred to herein as the "responsive layers". It should be noted that these layers may be cooperatively responsive to a ligand, or may be independently responsive to different ligands. Layer 12 located between responsive layers 11 and 13 is a fusible layer which is fusible under the conditions of ultrasonic or laser energy utilized herein and capable of bonding or welding to each of layers 11 and 13 to form an integral element.

FIG. 2 illustrates a test element 14 which has been cut from composite blank 10. Each of the responsive layers 11 and 13 has become bonded by the welding action of laser or ultrasonic energy which melts fusible layer 12 and fuses the layers together along their respective cut edges.

FIG. 3 illustrates in a schematic manner the formation of a composite blank from fibrous responsive layers 11 and 13 and fusible layer 12. The composite blank 10 then is subjected to ultrasonic or laser cutting along the dashed lines 15 which are dimensioned in accordance with the desired size and number of test elements. In subjecting composite 10 to the action of suitable ultrasonic or laser energy along dashed lines 15, the test elements 14 are cut and simultaneously welded along their adjacent edges only to form an integral element 14 as the ultimate product. The interior adjacent surfaces are not welded and remain unadhered. This test element can be used as is, or it can be mounted on a substrate carrier support, stick or holder.

The composite can also be formed in such a manner that the bottom most layer 13 is an inert carrier support layer. The dimensions can also be varied so that each layer is not identical in size. For example, if layer 13 is a base support member, then the other two or more layers can be smaller so that when the test element is cut the base support carrier or holder can extend out beyond the end of the test element.

FIG. 4 schematically illustrates how the test element is cut from the composite blank employing an ultrasonic apparatus. In carrying out the invention, the composite blank is fed to the apparatus such as a high power output Branson Probe type sonicator having a flat, carbide tipped horn 16 and a hardened steel cutting edge 17. Horn or probe 16 is a one-half wavelength long resonant bar or metal section that transfers vibratory energy to the workpiece which undergoes a small amplitude oscillation at, for example, 20 KHz. In addition to the mechanical cutting action that takes place, a considerable amount of heating occurs in a highly specific focused zone sufficient to melt the thermoplastic layer along the cutting edge to fuse the thermoplastic layer to the adjacent ligand responsive layer. Thus, when the energy stops the molten material solidifies and a weld is achieved.

The base support member utilized in combination with the present test device can take on many variations in shape, size and material of construction. For example, it might be constructed of any substantially liquid impervious material, such as polystyrene, polyolefin, polyester, polyamide, glass, paper, wood, cardboard, metal or other material. Usually, however, it is preferred that the base member be of a polymeric material such as cellulose acetate, polyethylene terephthalate, etc. and especially polystyrene manufactured by Dow Chemical Company and known as Trycite ®. For most purposes it has been found preferable that the support member be relatively rigid and extend sufficiently far from the reagent layer position to afford the user a convenient handle.

When employing a plurality of layers 11 and 13, it is possible for one or more of such layers to be of absorbent material having the capability of being wettable by the test sample. In the case where the liquid test sample is aqueous, both synthetic and natural paper-like materials have been found to be useful. Typical of these materials are Lexon ® L-5418, (a rayon, acetate, cotton blend), Novonette ® 9603 (a rayon/polyolefin blend), and Webril ® M-1165 (cotton), all of which are manufactured by the Fiber Products Division of the Kendall Co. of Boston, Mass.; products from the C. H. Dexter Division of the Dexter Corporation known as X-2526 (nonwoven rayon fibers), 1235 (rayon/thermoplastic fiber blend), and 1148-T (blend of cellulose fibers); and, from Mead Paper Specialities of South Lee, Mass., paper products, designated as 739,469 and 624.

Generally, the reagent containing layer (responsive layer) is filter piper, cloth, felt, porous ceramic, woven or matted glass fibers, polyamide fibers, and other materials known in the art for use in reagent strip analytical devices. Whatman filter paper W54, W3MM and W31ET are especially preferred. Whichever substance is chosen (for example, absorbent paper), it is incorporated with an indicator reagent system responsive to the particular test sample constituent being analyzed. Thus, if the reagent layer is to be responsive to glucose it could be incorporated with a glucose oxidase enzyme, a peroxidase enzyme and o-tolidine. Such a reagent system turns blue when contacted with a liquid sample containing glucose. The selection of the proper reagent layer material and indicator is well within the skill of the art and is easily determined in accordance with known reagent strip considerations of intended use and manufacturing requirements.

Multilayer test strips of the prior art have generally been prepared by spraying or otherwise applying an adhesive onto a plastic or paper support member and then adhering one or more reagent containing layers utilizing a variety of adhesive materials. Some test strips have simply used the expedient of stapling a plurality of test strips together. Thus, in Anderson, U.S. Pat. No. 3,511,608, inert sheets are interposed between the plurality of reagent test strips to prevent the chemicals from reacting prematurely. Then when the test is ready to be carried out, the inert strips are removed in order to avoid interference with the actual determination. Cement, glue or other adhesive material have also been used for this purpose.

In other developments, a mesh of thermoplastic material, for example, is used to adhere the test paper to a support (U.S. Pat. No. 3,802,842), or a test paper is sealed between wwo thermoplastic layers and bonded to a holder (U.S. Pat. No. 4,061,468).

The present invention provides a multilayer analytical test element comprising a plurality of layers which are cooperatively responsive to detect a ligand in a liquid sample, or to detect the ligand binding capacity of the sample, to give a detectable response. The layers include at least one layer that is responsive as described above and a second layer that is fusible when subjected to ultrasonic or laser energy and positioned adjacent each other. The layers are first assembled in the desired configuration to form a composite blank consisting of a plurality of unadhered layers from which is cut one or more test elements. The composite blank is larger in dimensions than the ultimate test element and can be in the form of a large pad or stock which is then cut into one or more test elements.

In a further aspect of the invention, the invention provides a multilayer analytical test element wherein a plurality of paper or other absorbent layers alternate with thermoplastic permeable material positioned between said paper layers, at least one of the paper or absorbent layers being impregnated with a selected reagent wherein the paper layers are bonded together at their respective edges only by said thermoplastic permeable material by the cutting action of ultrasonic or laser energy. The thermoplastic material can, if desired, have a configuration with a center opening, e.g., a square opening, which permits the unimpaired flow of liquid through the layers while having theromplastic material present at the edges for bonding purposes.

The present invention is carried out by ultilizing an ultrasonic or laser cutting device to simultaneously cut a multilayer analytical test element of specified dimensions from a larger pad or composite material and at the same time weld the plurality of cut layers together along the cutting edge to produce the desired test devices. During the cutting operation utilizing the ultrasonic or laser energy, a slight edge melting occurs in the thermoplastic layer which is sufficient to cement or bond the multilayered materials together. It is believed the thermoplastic layer migrates or slightly diffuses into the porous edge surfaces of the responsive layers and upon cooling thereby bonds adjacent layers together. In preparing the large pad or composite blank material, alternating paper layers can be arranged with a thermoplastic screen-like material or mesh in a sandwich configuration which permits incompatible reagents to be separately incorporated into each paper layer. The intermediate layer of thermoplastic mesh can prevent premature contact of reagents in the respective paper layers. The technique can also be used to incorporate a mesh overlayer over a reagent film or paper layer to obtain a laminated product. In this manner, a composite blank material or large pad of alternating layers can be formed. The dimensions of this pad can be such that the surface area thereof permits a plurality of analytical test elements to be cut therefrom according to the desired size and shape. It is also possible to dimension the pad such that it is slightly larger in surface area than the desired test element so that only one test element is cut from the composite of test layer and plastic screen. The reagent impregnated layers used in accordance with the invention are conventional ones such as those described above.

The mesh layer can be any suitable thermoplastic mesh or screen and, for example, can be formed of regularly woven filaments in the form of a fabric having both weft and warp threads. It can also be in the form of an unwoven fabric. Also possible is the use of thin felt or fleece-like mesh of sufficient stability in which the fiber structure is non-uniform. Synthetic resin fabrics formed of monofilaments or spun filaments are especially suitable. Typically, the mesh or screen layer can be formed of thermoplastic synthetic resins such as the polyamides (nylon), polyesters, polyethylene, polypropylene, PVC and a large variety of polymers and copolymers. Preferably, the mesh will have openings of between about 10 and about 1000 microns. In addition, membranes having pore openings ranging from about 0.1 to about 100 microns can be used. Especially preferred are polycarbonate membranes from nucleopore membrane of Pleasanton, Calif., Verspor membrane from Gelman of Ann Arbor, Mich. and nylon membranes from Pall Ultrafine Filtration Corp. of Cortland, N.Y. It is also possible to use colored materials and to impregnate the synthetic resin mesh with any other materials depending upon the analytical test to be ultimately carried out. The important quality that these materials must possess is that of being fusible (meltable or softenable) under the temperature conditions achieved by the ultrasonic or laser energy so that they will be capable of welding the several layers together.

Generally, the responsive layer or reagent containing layer will be pervious; that is, absorbent or somewhat porous at least to the extend to enable the softened fusible layer to partially migrate therein to thereby enable upon hardening a good weld to form between the fusible layer and the reagent containing layer adjacent thereto.

In preparing the test strips in accordance with the invention, the plurality of layers which are cooperatively responsive to detect a ligand in a ligand sample, or to detect the ligand binding capacity of the sample, can be arranged in the desired configuration, typically alternating with the thermoplastic layer. It should be noted that the present invention contemplates a single reagent layer and a single thermoplastic layer used together above, or with an inert support material or carrier which can be plastic such as PVC, polystyrene or any other suitable support. These supports can be opaque, translucent or transparent to light or other energy as desired and depending upon the particular test to be utilized. The mesh layer and the other layers e.g., paper layers and reagent impregnated layers are arranged one on top of the other in the desired orientation to form a composite of layers which can be referred to as the composite blank material or pad. The dimensions of the various layers are not critical and can vary as desired or convenient. Usually each layer is of the same general size as the adjacent layer although depending on the geometry and configuration of the ultimate test strip this can be varied as well. In a typical embodiment, the multilayer composite blank is somewhat larger than the final test strip so as to enable the test strip to be cut from the composite blank according to the desired dimensions. In like manner, the composite blank can be of sufficiently larger surface area to permit a multiplicity of test strips to be cut from the composite blank.

After assembling the plurality of layers into the composite blank, the individual layers are not adhered to each other at this point. The composite blank is then fed to the ultrasonic or laser cutter device. This device will automatically orient the cuts to be made in a series of parallel cuts of the desired size so that the composite blank material can then be cut into the desired number of test strips of the desired dimensions. While the cutting is taking place, a slight melting of the fusible layer simultaneously takes place at its edges whereby the fusible mesh layer functions to bond the paper layer or other reagent impregnated layers to each other at the edges thereof to form welds along the edge of the plurality of layers. This results in welding the plurality of layers into the integral test strip of the desired dimensions.

A variety of ultrasonic devices can be utilized in accordance with the present invention. The one that has been found to be particularly desirable is the one known as the Branson Probe type sonicator. In this device, a flat, carbide-tipped horn undergoes small amplitude oscillations at about 20 KHz. The composite blank of layered material to be cut into the desired test strips is fed between the face of the sonicator and a hardened steel stationary cutting edge. In addition to the mechanical cutting action that takes place, there is a considerable localized heating which is sufficient to melt a number of suitable plastics and generally leave a slightly heat rounded edge. The welding of the layers that takes place occurs at the edges of the layers. The interior surfaces are not fused together. The lack of interior melting or fusing of the thermoplastic layer means that nothing will interfere with the proper functioning of the test layers which may depend on a flow of substances between layers for the proper test to be made. This device easily cuts polyester, polyethylene, Trycite, paper, laminated paper and paper/Trycite/paper laminates.

Ultrasonic welding and means for bonding thermoplastic sheet material is, of course, known in the art as may be seen from such prior art as U.S. Pat. No. 3,505,136 which shows a method and apparatus for electronically bonding thermoplastic material. This system includes a vibratory heat sealing tool having a jaw member or horn which is vibrated at its natural mechanical resonance frequency through the use of a crystal or other transducer. The pieces of material to be joined are inserted between the vibrating jaw and a stationary jaw to provide an uniform and continuous seal. Generally, sound velocity in plastic materials ranges from hundreds to thousands of meters per second so that a sound wave applied to a plastic material having a frequency in the range of 10 kilocycles to 10 megacycles per second will have a wave length in the interior of the plastic materials which is on the order of millimeters or less with the consequence that it obtains an appreciable directivity. Ultrasonics can then be focused with a frequency within the above range to the interior or surface of a plastic member so as to produce a sharp focal zone having a high density of acoustic energy and thereby limiting the area wherein heat is produced to the focal zone. This results in an ability to carefully focus the cutting tool and the welding effect and not adversely affect any heat sensitive materials such as reagents impregnated in the test strip. The resulting test devices do not exhibit the deformation which can occur with the compression of the conventional slitting procedure used to form reagent test devices.

Ultrasonic devices used can have a high frequency above 10 kilocycles per second in order to assure maximum absorption by plastic materials to be worked and positive focusing to attain a relatively sharp focal zone. Suitable vibrators for this purpose can be formed from various known materials capable of being excited to effect resonance at such high frequency, for example, electrostrictive materials such as barium titanate and lead zirconate, or piezoelectric materials such as quartz. Below 10 kilocycles, there occurs a difficulty in efficiently focusing ultrasonics. The upper limit of the frequency range is principally determined by the availability of vibrator materials and construction requirements for mechanical strength. An ultrasonic apparatus for welding plastic materials is shown in U.S. Pat. No. 3,573,139.

Another example of an ultrasonic tool is shown in U.S. Pat. No. 3,562,041. Methods for bonding a plurality of webs together while they are being formed in juxtaposed relation at a particular predetermined velocity along a predetermined path is also known in the art as shown by U.S. Pat. No. 4,404,052.

Other types of sheet materials have also been welded together by use of ultrasonics as shown in U.S. Pat. No. 4,313,774.

The following examples illustrate the present invention without limiting it in any respect.

EXAMPLE 1

Utilizing a paper sheet known as "W31ET" (manufactured by Whatman, Inc., Clifton, N.J.), a composite blank of a sheet of this paper on Trycite was prepared. Trycite is polystyrene manufactured by Dow Chemical Co. The composite was then cut by a Branson Probe type sonicator with an amplitude oscillation at 20 KHz. The composite of the Trycite and the paper was fed between the face of the horn and the hardened steel stationary cutting edge. This was cut into test strips approximately 1" by ¾". An examination of the product showed that the paper was welded to the Trycite at the edge of the cuts.

EXAMPLE 2

Utilizing the same procedure as set forth in Example 1, a double pad of W31ET paper was formed by placing two sheets of the W31ET paper together and placing a Trycite sheet mesh in the center. The same sonicator was used under the same conditions. An examination of the test strips that were cut from the large sheets showed that the welding of both sheets of paper to the Trycite occurred at the edge of the cut. Thus, a double pad system was created where only the edges of the material were welded.

Following the procedures set forth above, a variety of test strips can be prepared wherein the paper sheet is impregnated with a variety of reagent compounds such as those described in U.S. Pat. No. 4,390,343 and 4,301,115.

By utilizing the ultrasonic or laser cutting and welding process as described herein, it is possible to form test strips of the type where one or more responsive layers are formed into a composite with an inert carrier substrate and the top most ligand responsive layer has placed over it the thermoplastic fusible layer. The composite is then cut into the desired dimensions of the test element or plurality of test elements. Simultaneously therewith, the top thermoplastic fusible layer is welded to the adjacent ligand responsive layer. If there are a plurality of fusible layers and ligand responsive layers, the cutting and welding will simultaneously result in welding all layers together and to the inert cover layer. Alternately, the ligand responsive layers can be welded together in this manner and then adhered to a suitable inert carrier or holder device by conventional techniques, including the use of double faced adhesive tape known as double sticks, available from the 3M Company.

One advantage of employing a laser over ultrasonic equipment is that the laser head never contacts the layers which are cut and welded together. Accordingly, the laser head does not become dirty.

Further variations and modifications of the invention will become apparent to those skilled in the art from a reading of the foregoing and are intended to be encompassed by the claims appended hereto.

What is claimed is:

1. A method of making a multilayer analytical test element comprising a plurality of layers containing a single reagent layer which detects a ligand in, or detects the ligand binding capacity of, a liquid sample, and at least one of said layers is a fusible layer, which method comprises arranging said layers in an unadhered assembly with one layer on top of the other to form a composite blank of said layers, and subjecting said composite blank of said layers to ultrasonic or laser energy to simultaneously bond together the layers at each respective edge thereof while cutting said element from said composite blank of layers such that the fusible layer partially migrates into the reagent layer where the layers are bonded.

2. The method of claim 1 in which the energy is ultrasonic energy.

3. The method of claim 1 in which the energy is laser energy.

* * * * *